United States Patent [19]

Schuda et al.

[11] Patent Number: 4,831,165

[45] Date of Patent: May 16, 1989

[54] HYDROGENATION PROCESS FOR THE FORMATION OF 3,4-DIHYDRO HMG-COA REDUCTASE INHIBITORS

[75] Inventors: Ann D. Schuda, New Providence; Thomas R. Verhoeven, Cranford; Ichiro Shinkai, Westfield, all of N.J.

[73] Assignee: Merck & Co., Inc., Rahway, N.J.

[21] Appl. No.: 92,804

[22] Filed: Sep. 3, 1987

[51] Int. Cl.⁴ .................. C07D 309/30; C07F 7/18
[52] U.S. Cl. ................... 549/214; 549/292
[58] Field of Search .................. 549/214, 292

[56] References Cited

U.S. PATENT DOCUMENTS 4,351,844  9/1982  Patchett et al. ............. 549/292

OTHER PUBLICATIONS

Smith et al., "Homogeneous Catalytic, etc", TL (7) 525 (1970).
Biellmann et al., "Homogeneous Phase, etc", CA 66: 104500s.
Kuo et al., J. Org. Chem., 48, 1991 (1983).

Primary Examiner—Richard L. Raymond
Attorney, Agent, or Firm—Melvin Winokur; Joseph F. DiPrima

[57] ABSTRACT

A novel hydrogenation process using a homogenous rhodium catalyst for selectively reducing the 3,4 double bond in the polyhydronaphthyl ring of lovastatin, simvastatin or C-8-acyl or C-6-substituted analogs thereof is disclosed.

20 Claims, No Drawings

HYDROGENATION PROCESS FOR THE FORMATION OF 3,4-DIHYDRO HMG-COA REDUCTASE INHIBITORS

BACKGROUND OF THE INVENTION

Mevinolin, also known as Lovastatin is a potent HMG-CoA reductase inhibitor and as such is an effective antihypercholesterolemic agent. Patchett et al. (U.S. Pat. No. 4,351,844) have found that a 3,4-dihydrolovastatin analog (I) is also a potent HMG-CoA reductase inhibitor.

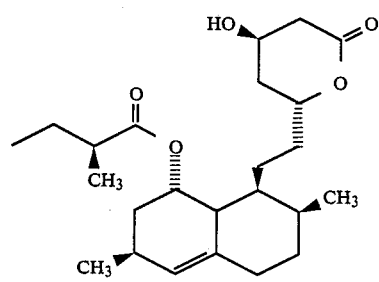

Patchett, supra, describe a catalytic hydrogenation process employing tris(triphenylphosphine) chlororhodium in an aromatic solvent for the reduction of lovastatin to compound (I). This process has also been described by Kuo et al., *J. Org. Chem.*, 48, 1991 (1983). The Patchett-Kuo process in an aromatic solvent requires a large excess (225 to 100 weight percent catalyst to lovastatin) of the expensive rhodium catalyst. This method also produces approximately 10 percent of the isomeric 3,5-dihydrolovastatin derivative (II) which required several recrystallizations and preparative HPLC for separation. When the Patchett-Kuo process is applied to synvinolin (simvastatin) 20 percent of the isomeric 3,5 dihydro simvastatin derivative is produced.

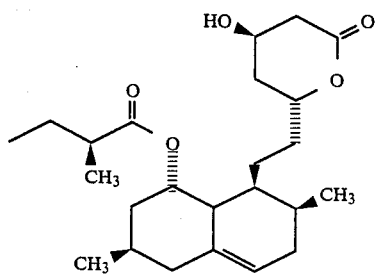

DETAILED DESCRIPTION OF THE INVENTION

The novel process of this invention may be depicted as:

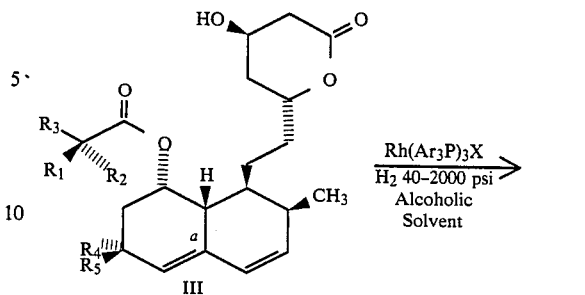

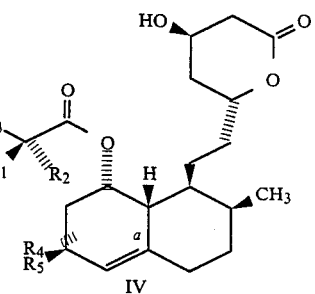

wherein:
$R_1$ is H or $C_{1-3}$alkyl;
$R_2$ is H or $C_{1-3}$alkyl;
$R_3$ is $C_{1-5}$alkyl, phenyl, or $C_{3-7}$ cycloalkyl; or $C_{1-5}$alkyl or phenyl substituted with a group Y where Y is a group not reduced by a triarylphosphine rhodium halide, examples of such a group Y are:
(a) OH or $t-C_4H_9(Me)_2SiO$
(b) halogen (F, Cl or Br);
(c) trifluoromethyl;
(d) $C_{1-3}$alkoxy;
(e) $C_{1-3}$alkylcarbonyloxy;
(f) phenylcarbonyloxy;
(g) $C_{1-3}$alkoxycarbonyl; or
(h) phenyloxycarbonyl;
$R_4$ is H or $CH_3$ or $CH_2OH$ or OH or $CH_2OSi(Me)_2t-C_4H_9$ or $OSi(Me)_2t-C_4H_9$;
$R_5$ is H or $CH_2OH$ or OH or $CH_2OSi(Me)_2t-C_4H_9$ or $OSi(Me)_2t-C_4H_9$; provided that when either $R_4$ or $R_5$ is $CH_2OH$ or $CH_2OSi(Me)_2t-C_4H_9$ the other is H; and one and only one of $R_4$ and $R_5$ can be OH or $OSi(Me)_2t-C_4H_9$;
Alternatively $R_4$ and $R_5$ may be represented as:
$R_4$ is H or $CH_3$ or $CH_2OH$ or $CH_2 OSi(Me)_2t-C_4H_9$;
$R_5$ is H or $CH_2OH$ or $CH_2OSi(Me)_2t-C_4H_9$; provided that at least one of $R_4$ or $R_5$ is H.
Ar is phenyl or naphthyl or $C_{1-3}$Alkoxy substituted phenyl or naphthyl;
X is Cl or Br;
Alcoholic Solvent is an alcohol such as isopropanol or ethanol or a mixture of such alcohol with a hydrocarbon such as benzene or toluene;
a is a double bond or a single bond.

The instant process selectively reduces the 3,4 double bond in the polyhydronaphthyl ring of lovastatin, simvastatin or 8-acyl or 6-substituted analogs thereof. A homogenous rhodium catalyst is able to discriminate between a double bond in the 3,4 and 4a,5 positions, complexing with and thus allowing hydrogenation of only the 3,4 double bond. Critical to the present invention is applicants' finding that an alcoholic co-solvent increases the catalyst lifetime which thus removes the necessity of large excesses of the expensive rhodium catalyst. The present reaction is typically conducted with a 5 weight percent of catalyst to olefinic substrate which contrasts with the very large excesses of catalyst required in the prior art reductions. Unexpectedly, inclusion of an alcoholic co-solvent also decreases substantially the amount of the "1,4-reduction" side product (e.g. II) which is produced. Formation of large proportions of this 3,5-dihydro side product is highly detrimental and seriously compromises the final product purity since it can co-crystallize with the desired product. This side product has previously been removed by a tedious HPLC procedure.

The invention may be practiced wherein $R_4$ or $R_5$ are unprotected $CH_2OH$ or OH moieties, however in some instances it may be preferable to protect OH with a hydroxyl protecting group such as tert-butyldimethylsilyl. Other protecting groups such as tert-butyldiphenylsilyl, trimethylsilyl, triethylsilyl, triisopropylsilyl and tetrahydropyranyl could be substituted for tert-butyldimethylsilyl without effecting the outcome of the instant invention.

One embodiment of the present invention is the preparation of compounds of structure (IV) wherein:
 $R_1$ is methyl,
 $R_2$ is H or $C_{1-3}$alkyl,
 $R_3$ is $C_{1-5}$alkyl, phenyl or $C_{3-7}$cycloalkyl; or $C_{1-5}$alkyl or phenyl substituted with a group Y where Y is a group not reduced by a triarylphosphine rhodium halide such as:
  (a) OH or $t-C_4H_9(Me)_2SiO$;
  (b) halogen (F, Cl or Br);
  (c) trifluoromethyl;
  (d) $C_{1-3}$alkoxy;
  (e) $C_{1-3}$alkylcarbonyloxy;
  (f) phenylcarbonyloxy;
  (g) $C_{1-3}$alkoxycarbonyl; or
  (h) phenyloxycarbonyl;
 $R_4$ is $CH_3$;
 $R_5$ is H; and
 a is a double bond.

In one class of this embodiment, $R_3$ is $C_{1-5}$alkyl. In a subclass are compounds (IV) wherein:
 a. $R_2$ is H, $R_3$ is $CH_3CH_2$;
 b. $R_2$ is $CH_3$, $R_3$ is $CH_3CH_2$.

A second embodiment is the preparation of compounds of structure (IV) wherein:
 $R_1$ is methyl,
 $R_2$ is H or $C_{1-3}$alkyl,
 $R_3$ is $C_{1-5}$alkyl, phenyl or $C_{3-7}$cycloalkyl; or $C_{1-5}$alkyl or phenyl substituted with a group Y where Y is a group not reduced by a triarylphosphine rhodium halide such as:
  (a) OH or $t-C_4H_9(Me)_2SiO$;
  (b) halogen (F, Cl or Br);
  (c) trifluoromethyl;
  (d) $C_{1-3}$alkoxy;
  (e) $C_{1-3}$carbonyloxy;
  (f) phenylcarbonyloxy;
  (g) $C_{1-3}$alkoxycarbonyl; or
  (h) phenyloxycarbonyl.
 $R_4$ is H or $CH_2OH$ or $CH_2OSi(Me)_2t-C_4H_9$;
 $R_5$ is H or $CH_2OH$ or $CH_2OSi(Me)_2t-C_4H_9$; provided that at least one of $R_4$ or $R_5$ is H.

In one class or this embodiment $R_2$ is H or $CH_3$ and $R_3$ is $CH_3CH_2$. In a subclass are compounds (IV) wherein:
 a. $R_2$ is H, $R_4$ is $CH_2OH$, $R_5$ is H;
 b. $R_2$ is H, $R_4$ is H, $R_5$ is $CH_2OH$;
 c. $R_2$ is $CH_3$, $R_4$ is $CH_2OH$, $R_5$ is H;
 d. $R_2$ is $CH_3$, $R_4$ is H, $R_5$ is $CH_2OH$.
 e. $R_2$ is H, $R_4$ is $CH_2OSi(Me)_2t-C_4H_9$, $R_5$ is H;
 f. $R_2$ is H, $R_4$ is H, $R_5$ is $CH_2OSi(Me)_2t-C_4H_9$;
 g. $R_2$ is $CH_3$, $R_4$ is $CH_2OSi(Me)_2t-C_4H_9$, $R_5$ is H;
 h. $R_2$ is $CH_3$, $R_4$ is H, $R_5$ is $CH_2OSi(Me)_2t-C_4H_9$.

A third embodiment is the preparation of compounds of structure (IV) wherein:
 $R_1$ is methyl,
 $R_2$ is H or $C_{1-3}$alkyl,
 $R_3$ is $C_{1-5}$alkyl, phenyl or $C_{3-7}$cycloalkyl; or $C_{1-5}$alkyl or phenyl substituted with a group Y where Y is a group not reduced by a triarylphosphine rhodium halide such as:
  (a) OH or $t-C_4H_9(Me)_2t-C_4H_9$;
  (b) halogen (F, Cl or Br);
  (c) trifluoromethyl;
  (d) $C_{1-3}$alkoxy;
  (e) $C_{1-3}$carbonyloxy;
  (f) phenylcarbonyloxy;
  (g) $C_{1-3}$alkoxycarbonyl; or
  (h) phenyloxycarbonyl.
 $R_4$ is H or $CH_3$ or OH or $OSi(Me)_2t-C_4H_9$;
 $R_5$ is H or OH or $OSi(Me)_2t-C_4H_9$; provided that when either $R_4$ or $R_5$ is OH or $OSi(Me)_2t-C_4H_9$ the other is H or $CH_3$.

In one class of this embodiment, $R_2$ is H or $CH_3$, and $R_3$ is $CH_3CH_2$. In a subclass are compounds (IV) wherein:
 a. $R_2$ is H, $R_4$ is OH and $R_5$ is H.
 b. $R_2$ is H, $R_4$ is H and $R_5$ is OH.
 c. $R_2$ is H, $R_4$ is $CH_3$ and $R_5$ is OH.
 d. $R_2$ is $CH_3$, $R_4$ is OH and $R_5$ is H.
 e. $R_2$ is $CH_3$, $R_4$ is H and $R_5$ is OH.
 f. $R_2$ is $CH_3$, $R_4$ is $CH_3$ and $R_5$ is OH.
 g. $R_2$ is H, $R_4$ is $OSi(Me)_2t-C_4H_9$ and $R_5$ is H.
 h. $R_2$ is H, $R_4$ is H and $R_5$ is $OSi(Me)_2t-C_4H_9$.
 i. $R_2$ is H, $R_4$ is $CH_3$ and $R_5$ is $OSi(Me)_2t-C_4H_9$.
 j. $R_2$ is $CH_3$, $R_4$ is $OSi(Me)_2t-C_4H_9$ and $R_5$ is H.
 k. $R_2$ is $CH_3$, $R_4$ is H and $R_5$ is $OSi(Me)_2t-C_4H_9$.
 l. $R_2$ is $CH_3$, $R_4$ is $CH_3$ and $R_5$ is $OSi(Me)_2t-C_4H_9$.

Starting olefin, lovastatin, wherein $R_1$ is methyl, $R_2$ is hydrogen, $R_3$ is ethyl, $R_4$ is methyl, $R_5$ is hydrogen and a is a double bond is readily available or may be prepared according to the fermentation procedures disclosed in U.S. Pat. No. 4,231,938. Simvastatin, wherein $R_1$ is methyl, $R_2$ is methyl, $R_3$ is ethyl, $R_4$ is methyl, $R_5$ is hydrogen and a is a double bond may be prepared from lovastatin following the procedure described in U.S. Pat. No. 4,582,915 or copending U.S. patent application Ser. No. 072,066 filed July 10, 1987.

Starting olefins wherein $R_4$ or $R_5$ is $CH_2OH$ are prepared following the procedure outlined in copending U.S. patent application Ser. No. 048,136 filed May 15, 1987.

Compounds wherein $R_4$ or $R_5$ is OH can be prepared following the descriptions in U.S. Pat. Nos. 4,517,373 and 4,537,859 for preparing the 6-hydroxyl derivatives. Protection of the 6-hydroxymethyl or the 6-hydroxy group can be accomplished following the procedure outlined in U.S. Pat. No. 4,444,784.

Dienes where both $R_4$ and $R_5$ are hydrogen may be prepared from the fermentation product compactin (also known as mevastatin) (Endo, et. al. *J. Antibiot*, 29, 1346 (1976)).

Starting olefins with substituted acyl groups are prepared using acyl chlorides, prepared by standard techniques, and the acylation procedure described by Hoffman et. al., in U.S. Pat. No. 4,444,784 or that disclosed in copending U.S. patent application Ser. No. 038,560 filed Apr. 15, 1987.

The rhodium catalyst is a tris(triaryl or substituted aryl phosphine) rhodium halide, preferably tris(triphenylphosphine) rhodium bromide or chloride, most preferably the chloride. The solvent is isopropanol or ethanol or a mixture of said alcohol with toluene or benzene or a like hydrocarbon. An example of such a mixture is 50—50 percent by volume isopropanol:toluene. The preferable solvent is isopropanol.

The olefinic substrate and the rhodium catalyst, in a weight percent ratio of about 5-75 weight percent catalyst to substrate, preferably about 5-25 percent, most preferably about 5 percent catalyst to substrate, are dissolved in the alcoholic solvent, at a temperature of 25° to 80° C., preferably 40° C. under hydrogen gas at a pressure of 40-1400 psi, preferably 600-1400 psi for about 25 hours. After standard workup procedures, evaporation of solvent gives a crystalline solid which can be recrystallized from ethyl acetate/hexanes to yield product containing less than 1 percent of olefin from a 1,4 reduction.

The following Examples illustrate the present invention and as such are not to be considered as limiting the invention set forth in the claims appended hereto.

EXAMPLE 1

Preparation of 6(R)-[2-[8(S)-(2,2-dimethylbutyryloxy)-2(S),6(R)-dimethyl-1,2,3,4,6,7,8,8a(S)-octahydro-1(S)]ethyl]-4(R)-hydroxy-3,4,5,6-tetrahydro-2H-pyran-2-one A solution of 6(R)-[2-[8(S)-(2,2-dimethylbutyryloxy)-2(S),6(R)-dimethyl-1,2,6,7,8,8a(R)-hexahydro-1(S)]ethyl]-4(R)-hydroxy-3,4,5,6-tetrahydro-2H-pyran-2-one (0.302 g, 0.722 mmol) and tris(triphenyl phosphine)rhodium (I) chloride (0.015 g, 0.016 mmol) in isopropanol (25 ml) was reduced at 40° C. under 1400 to 600 psi of $H_2$ for 25 hours. The solution was evaporated in vacuo and the residue taken up in diethyl ether and stirred. A precipitate formed. The slurry was vacuum filtered through a 1 inch bed of Florisil ® (Magnesium silicate filter aid used herein to retain any catalyst complex which remained in solution) and washed with 35 ml diethyl ether. The filtrate was evaporated in vacuo to a foamy glass. Further purification was achieved by short path silica gel chromatography (5-10 g silica gel/gram crude product) eluting with 1 percent isopropanol in dichloromethane. Evaporation of the appropriate fractions gave a white crystalline solid which was recrystallized from ethyl acetate/hexanes to give the title compound as white needles (m.p. 123°-123.5° C.). The product contained less than one percent of the "1,4 reduction" side product. HNMR (300 MHz, $CDCl_3$) δ 5.38 (m, 1H), 5.32 (m, 1H); 4.59 (m, 1H); 4.34 (m, 1H); 2.72 (dd, 1H, J=17.7, 5.4 Hz); 2.62 (m, 2H), 2.17-2.37 (m, 2H); 1.73-2.16 (m, 7H); 1.18-1.72 (m, 9H); 1.15 (s, 3H); 1.13 (s, 3H); 1.07 (d, 3H, J=7.5 Hz); 0.88 (d, 3H, J=7.5 Hz); 0.83 (t, 3H; J=7.5 Hz). The diagnostic olefinic signal of the "1,4 reduction" side product appears as a multiplet at δ 5.42-5.49.

EXAMPLES 2-12

Following the procedure substantially as described in Example 1 but substituting for Simvastatin, the starting olefin therein, approximately equimolar amounts of the compounds of structure (III) as described below there are prepared the 3,4-dihydro derivatives of (III).

|  | R1 | R2 | R3 | R4 | R5 | a |
|---|---|---|---|---|---|---|
| Example 2 | CH3 | H | CH3CH2 | CH3 | H | db |
| Example 3 | CH3 | CH3 | CH3CH2 | CH2OH | H | db |
| Example 4 | CH3 | CH3 | CH3CH2 | H | CH2OH | db |
| Example 5 | CH3 | H | CH3CH2 | CH2OH | H | db |
| Example 6 | CH3 | H | CH3CH2 | H | CH2OH | db |
| Example 7 | CH3 | H | CH3CH2 | OH | H | db |
| Example 8 | CH3 | CH3 | CH3CH2 | OH | H | db |
| Example 9 | CH3 | H | CH3CH2 | H | OH | db |
| Example 10 | CH3 | H | CH3CH2 | CH3 | OH | db |
| Example 11 | CH3 | CH3 | CH3CH2 | H | OH | db |
| Example 12 | CH3 | CH3 | CH3CH2 | CH3 | OH | db |
| Example 13 | CH3 | CH3 | CH3CH2 | CH2OSi(Me)2t-C4H9 | H | db |
| Example 14 | CH3 | CH3 | CH3CH2 | H | CH2OSi(Me)2t-C4H9 | db |
| Example 15 | CH3 | H | CH3CH2 | CH2OSi(Me)2t-C4H9 | H | db |
| Example 16 | CH3 | H | CH3CH2 | H | CH2OSi(Me)2t-C4H9 | db |
| Example 17 | CH3 | H | CH3CH2 | OSi(Me)2t-C4H9 | H | db |
| Example 18 | CH3 | CH3 | CH3CH2 | OSi(Me)2t-C4H9 | H | db |
| Example 19 | CH3 | H | CH3CH2 | H | OSi(Me)2t-C4H9 | db |
| Example 20 | CH3 | H | CH3CH2 | CH3 | OSi(Me)2t-C4H9 | db |
| Example 21 | CH3 | CH3 | CH3CH2 | H | OSi(Me)2t-C4H9 | db |
| Example 22 | CH3 | CH3 | CH3CH2 | H | OSi(Me)2t-C4H9 | db |

What is claimed is:

1. A process for the preparation of a compound of structural formula (IV):

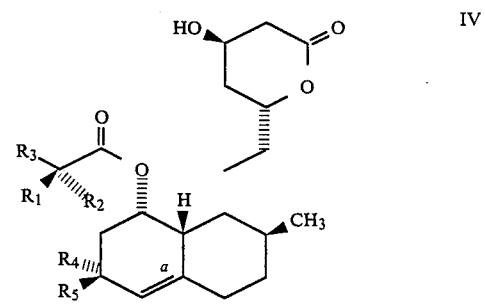

wherein:
$R_1$ is H or $C_{1-3}$alkyl;
$R_2$ is H or $C_{1-3}$alkyl;
$R_3$ is $C_{1-5}$alkyl, phenyl, or $C_{3-7}$ cycloalkyl; or $C_{1-5}$alkyl or phenyl substituted with a group Y where Y is selected from the group consisting of:
  (a) OH or t-$C_4H_9(Me)_2$SiO;
  (b) halogen;
  (c) trifluoromethyl;

(d) $C_{1-3}$alkoxy;
(e) $C_{1-3}$alkylcarbonyloxy;
(f) phenylcarbonyloxy;
(g) $C_{1-3}$alkoxycarbonyl; or
(h) phenyloxycarbonyl;

$R_4$ is H or $CH_3$ or $CH_2OH$ or OH or $CH_2OSi(Me)_2t$-$C_4H_9$ or $OSi(Me)_2t$-$C_4H_9$;

$R_5$ is H or $CH_2OH$ or OH or $CH_2OSi(Me)_2t$-$C_4H_9$ or $OSi(Me)_2t$-$C_4H_9$; provided that when either $R_4$ or $R_5$ is $CH_2OH$ or $CH_2OSi(Me)_2t$-$C_4H_9$ the other is H; and one and only one of $R_4$ and $R_5$ can be OH or $OSi(Me)_2t$-$C_4H_9$.

a is a double bond or a single bond;
which comprises: contacting of a compound of structural formula (IIi):

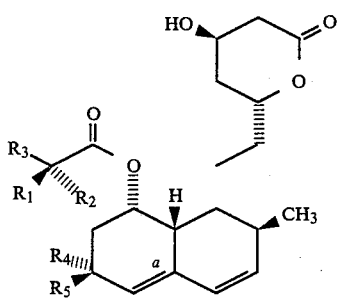

with $Rh(Ar_3P)_3X$; wherein
Ar is phenyl or naphthyl or $C_{1-3}$alkoxy substituted phenyl or naphthyl;
X is Cl or Br;
in an alcoholic solvent, under hydrogen gas at a pressure of 40–1400 psi at a temperature of 40°–80° C.

2. A process of claim 1 wherein the alcoholic solvent is a mixture of isopropanol or ethanol and a hydrocarbon such as benzene or toluene.

3. A process of claim 2 wherein the alcoholic solvent is isopropanol, or ethanol.

4. A process of claim 3 wherein the Rhodium Catalyst is $Rh(Ph_3P)_3Cl$.

5. A process of claim 4 wherein the weight percent ratio of catalyst to substrate (III) is about 5 weight percent.

6. A process of claim 5 wherein the hydrogen gas is at a pressure of about 600–1400 psi.

7. A process of claim 1 wherein $R_4$ is H or $CH_3$ or $CH_2OH$ or $CH_2OSi(Me)_2t$-$C_4H_9$; $R_5$ is H or $CH_2OH$ or $CH_2OSi(Me)_2t$-$C_4H_9$; provided that at least one of $R_4$ or $R_5$ is H.

8. A process of claim 1 wherein:
$R_1$ is $CH_3$,
$R_2$ is H or $CH_3$,
$R_3$ is $C_{1-5}$alkyl,
$R_4$ is $CH_3$,
$R_5$ is H,
a is a double bond.

9. A process of claim 8 wherein: $R_2$ is H and $R_3$ is $CH_3CH_2$.

10. A process of claim 8 wherein: $R_2$ is $CH_3$ and $R_3$ is $CH_3CH_2$.

11. A process of claim 1 wherein:
$R_1$ is $CH_3$,
$R_2$ is H or $CH_3$,
$R_3$ is $C_{1-5}$alkyl,
$R_4$ is H or $CH_2OH$ or $CH_2OSi(Me)_2t$-$C_4H_9$,
$R_5$ is H or $CH_2OH$ or $CH_2OSi(Me)_2t$-$C_4H_9$; and
a is a double bond.

12. A process of claim 11 wherein the compound (IV) prepared is selected from the group wherein:

| a. | $R_2$ is H, $R_3$ is $CH_3CH_2$, $R_4$ is $CH_2OH$, $R_5$ is H; | e. | $R_2$ is H, $R_3$ is $CH_3CH_2$, $R_4$ is $CH_2OSi(Me)_2t$-$C_4H_9$, $R_5$ is H; |
|---|---|---|---|
| b. | $R_2$ is H, $R_3$ is $CH_3CH_2$, $R_4$ is H, $R_5$ is $CH_2OH$; | f. | $R_2$ is H, $R_3$ is $CH_3CH_2$, $R_4$ is H, $R_5$ is $CH_2OSi(Me)_2t$-$C_4H_9$; |
| c. | $R_2$ is $CH_3$, $R_3$ is $CH_3CH_2$, $R_4$ is $CH_2OH$, $R_5$ is H; | g. | $R_2$ is $CH_3$, $R_3$ is $CH_3CH_2$, $R_4$ is $CH_2OSi(Me)_2t$-$C_4H_9$, $R_5$ is H; |
| d. | $R_2$ is $CH_3$, $R_3$ is $CH_3CH_2$, $R_4$ is H, $R_5$ is $CH_2OH$. | h. | $R_2$ is $CH_3$, $R_3$ is $CH_3CH_2$, $R_4$ is H, $R_5$ is $CH_2OSi(Me)_2t$-$C_4H_9$. |

13. A process of claim 1 wherein:
$R_1$ is $CH_3$,
$R_2$ is H or $CH_3$,
$R_3$ is H or $CH_3$ or OH or $OSi(Me)_t$-$C_4H_9$,
$R_5$ is H or OH or $OSi(Me)_2t$-$C_4H_9$; provided that one and only one of $R_4$ and $R_5$ is OH or $OSi(Me)_2t$-$C_4H_9$.

14. A process of claim 13 wherein $R_3$ is $C_{1-3}$alkyl.

15. A process of claim 14 wherein $R_3$ is $CH_3CH_2$.

16. A process of claim 15 wherein the compound (IV) prepared is selected from the group wherein:
a. $R_2$ is H, $R_4$ is OH and $R_5$ is H;
b. $R_2$ is $CH_3$, $R_4$ is OH and $R_5$ is H;
c. $R_2$ is H, $R_4$ is H and $R_5$ is OH;
d. $R_2$ is H, $R_4$ is $CH_3$ and $R_5$ is OH;
e. $R_2$ is $CH_3$, $R_4$ is H and $R_5$ is OH;
f. $R_2$ is $CH_3$, $R_4$ is $CH_3$ and $R_5$ is OH.
g. $R_2$ is H, $R_4$ is $OSi(Me)_2t$-$C_4H_9$ and $R_5$ is H;
h. $R_2$ is $CH_3$, $R_4$ is $OSi(Me)_2t$-$C_4H_9$ and $R_5$ is H;
i. $R_2$ is H, $R_4$ is H and $R_5$ is $OSi(Me)_2t$-$C_4H_9$;
j. $R_2$ is H, $R_4$ is $CH_3$ and $R_5$ is $OSi(Me)_2t$-$C_4H_9$;
k. $R_2$ is $CH_3$, $R_4$ is H and $R_5$ is $OSi(Me)_2t$-$C_4H_9$;
l. $R_2$ is $CH_3$, $R_4$ is $CH_3$ and $R_5$ is $OSi(Me)_2t$-$C_4H_9$.

17. A process of claim 9 wherein the alcoholic solvent is isopropanol, the catalyst is tris(triphenylphosphine)rhodium (I) chloride at a weight percent ratio of 5 percent catalyst to substrate (III), under a hydrogen gas pressure of about 1400 psi at a temperature of about 40° C.

18. A process of claim 10 wherein the alcoholic solvent is isopropanol, th catalyst is tris(triphenylphosphine)rhodium (I) chloride at a weight percent ratio of 5 percent catalyst to substrate (III), under a hydrogen gas pressure of about 1400 psi at a temperature of about 40° C.

19. A process of claim 12 wherein the alcoholic solvent is isopropanol, the catalyst is tris(triphenylphosphine)rhodium (I) chloride at a weight percent ratio of 5 percent catalyst to substrate (III), under a hydrogen gas pressure of about 1400 psi at a temperature of about 40° C.

20. A process of claim 16 wherein the alcoholic solvent is isopropanol, the catalyst is tris(triphenylphosphine)rhodium (I) chloride at a weight percent ratio of 5 percent catalyst to substrate (III), under a hydrogen gas pressure of about 1400 psi at a temperature of about 40° C.

* * * * *

UNITED STATES PATENT AND TRADEMARK OFFICE
CERTIFICATE OF CORRECTION

PATENT NO. : 4,831,165

DATED : May 16, 1989

INVENTOR(S) : Ann E. DeCamp, et al.

It is certified that error appears in the above-identified patent and that said Letters Patent is hereby corrected as shown below:

On the title page, Item [75], "Ann D. Schuda" should be --Ann E. DeCamp--.

Signed and Sealed this

Seventeenth Day of October, 1989

Attest:

DONALD J. QUIGG

Attesting Officer

Commissioner of Patents and Trademarks

UNITED STATES PATENT AND TRADEMARK OFFICE
CERTIFICATE OF CORRECTION

PATENT NO. : 4,831,165
DATED : May 16, 1989
INVENTOR(S) : A. Schuda et al

It is certified that error appears in the above-identified patent and that said Letters Patent is hereby corrected as shown below:

In Claim 13, line 24, "$R_3$ is H or $CH_3$ or OH or $OSi(Me)_2 t\text{-}C_4H_9$" should be deleted and --$R_4$ is H or $CH_3$ or OH or $OSi(Me)_2 t\text{-}C_4H_9$-- should be inserted therefor.

Signed and Sealed this

Thirteenth Day of March, 1990

*Attest:*

JEFFREY M. SAMUELS

*Attesting Officer*     *Acting Commissioner of Patents and Trademarks*